(12) United States Patent
Tano

(10) Patent No.: US 7,666,190 B2
(45) Date of Patent: Feb. 23, 2010

(54) HOLDER OF CONTACT LENS FOR VITREOUS BODY OPERATION, AND HOLDING PART AND CONNECTION PART OF CONTACT LENS FOR VITREOUS BODY OPERATION

(75) Inventor: Yasuo Tano, Kobe (JP)

(73) Assignee: Hoya Healthcare Corporation, Tokyo (JP)

(*) Notice: Subject to any disclaimer, the term of this patent is extended or adjusted under 35 U.S.C. 154(b) by 410 days.

(21) Appl. No.: 10/088,874

(22) PCT Filed: Dec. 19, 2001

(86) PCT No.: PCT/JP01/11135
§ 371 (c)(1),
(2), (4) Date: Jun. 11, 2002

(87) PCT Pub. No.: WO03/000160
PCT Pub. Date: Jan. 3, 2003

(65) Prior Publication Data
US 2003/0109885 A1 Jun. 12, 2003

(30) Foreign Application Priority Data
Jun. 21, 2001 (JP) .............................. 2001-188253

(51) Int. Cl.
*A61F 9/00* (2006.01)
(52) U.S. Cl. ...................................... 606/107; 600/236
(58) Field of Classification Search .............. 606/107, 606/166, 236, 201, 206, 215, 218, 235; 623/6.12
See application file for complete search history.

(56) References Cited

U.S. PATENT DOCUMENTS

| 2,702,540 A | * | 2/1955 | Debeh | 600/218 |
| 2,845,925 A | * | 8/1958 | Jayle | 600/233 |
| 3,139,298 A | * | 6/1964 | Grabiel | 606/107 |
| 3,680,546 A | * | 8/1972 | Asrican | 600/219 |
| 3,943,981 A | * | 3/1976 | De Brabander | 24/445 |

(Continued)

FOREIGN PATENT DOCUMENTS

EP 0 608 052 A2 7/1994

(Continued)

OTHER PUBLICATIONS

Notice of Reason for Rejection mailed from the Japanese Patent Office on Sep. 30, 2003.

*Primary Examiner*—Michael J. Milano
*Assistant Examiner*—Victor X Nguyen
(74) *Attorney, Agent, or Firm*—Oliff & Berridge, PLC

(57) ABSTRACT

In surgery of the vitreous body in an eyeball of a human body, a burden on and time of a surgeon is suppressed from being spent, a burden on the eyeball of a patient is greatly reduced, and further, the possibility of a complication after the surgery is also lessened. A holding apparatus, which has eyelid opener portions for pulling and opening upper and lower eyelids, a lens ring for holding a surgical contact lens on the eyeball, and connecting portions for connecting the eyelid opener portions with the lens ring of the surgical contact lens so that the surgical contact lens is held on the eyeball, is set on the eyeball of the patient, which makes it unnecessary to stitch of the lens ring on the eyeball.

5 Claims, 13 Drawing Sheets

U.S. PATENT DOCUMENTS

| | | | | |
|---|---|---|---|---|
| 4,037,589 | A | * | 7/1977 | McReynolds ............... 600/209 |
| 4,145,013 | A | * | 3/1979 | Waller ........................ 242/586 |
| 4,300,244 | A | * | 11/1981 | Bokros ...................... 623/1.13 |
| 5,054,906 | A | * | 10/1991 | Lyons, Jr. ................... 351/205 |
| 5,171,254 | A | * | 12/1992 | Sher ........................... 606/166 |
| 5,341,798 | A | * | 8/1994 | Grounauer ................. 600/236 |
| 5,556,417 | A | * | 9/1996 | Sher ........................... 600/236 |
| 5,618,261 | A | * | 4/1997 | Nevyas ....................... 600/236 |
| 5,762,606 | A | | 6/1998 | Minnich |
| 5,938,674 | A | | 8/1999 | Terry |
| 6,092,898 | A | * | 7/2000 | de Juan, Jr. ................. 351/177 |

FOREIGN PATENT DOCUMENTS

| | | |
|---|---|---|
| JP | 43-20636 | 8/1968 |
| JP | A 7-501247 | 2/1995 |
| JP | A 10-216193 | 8/1998 |
| WO | WO 92/07501 | 5/1992 |
| WO | WO 93/09719 | 5/1993 |
| WO | WO 99/20171 | 4/1999 |
| WO | WO 00/02080 | 1/2000 |

* cited by examiner

Related Art

Related Art

HOLDER OF CONTACT LENS FOR VITREOUS BODY OPERATION, AND HOLDING PART AND CONNECTION PART OF CONTACT LENS FOR VITREOUS BODY OPERATION

TECHNICAL FIELD

The present invention relates to a holding apparatus for a vitreous body surgical contact lens (hereinafter referred to as surgical lens) which is used in diagnosis and surgery of an eyeball of a human body, for holding the surgical lens on the eyeball of the human body, and a holding portion and a connecting portion for the vitreous body surgical contact lens.

BACKGROUND ART

In the surgery of the eyeball of the human body, the surgical lens is indispensable in order to secure an excellent surgical field. Hereinafter, the surgical lens will be explained with reference to FIG. 12, FIGS. 13(A) and (B), and FIG. 14, taking a case of the vitreous body surgery, which is typical ophthalmologic surgery, as an example.

Incidentally, the same symbols and numerals are assigned to corresponding parts in FIG. 1 to FIG. 14.

In the vitreous body surgery, first of all, as shown in FIG. 12, an upper eyelid 110 and a lower eyelid 120 of an eyeball 100 of a patient laid on its back are pulled upward and downward respectively to be opened using eyelid openers 10.

Next, a surgical lens 50 is held in a desired position on the eyeball 100 whose eyelids are opened. However, since the eyeball 100 is substantially spherical, the surgical lens 50 is needed to be held so as not to slip down the eyeball.

Thus, as shown in FIG. 12, a surgical lens holding portion 30 (hereinafter referred to as lens ring 30) having a ring shape is conventionally stitched to a sclera 130 (the white part of the eyeball) on the eyeball 100 using a suture 60 in order to hold the surgical lens 50 on the eyeball.

This stitching will be further detailed using FIGS. 13(A) and (B), and FIG. 14.

FIG. 13(A) is a case in which the lens ring 30 having two stitching and engaging portions 35 is stitched on the eyeball 100, FIG. 13(B) is a case in which the lens ring 30 having four stitching and engaging portions 36 and 37 is stitched on the eyeball 100, and FIG. 14 is a cross-sectional view taken along the C-C line in the case.

Here, as shown in FIGS. 13(A) and (B), the lens ring 30 has a diameter larger than that of a cornea 131 and is held on the sclera 130. As the suture 60 for stitching the lens ring 30 on the sclera 130, a 5-0 Dacron suture or a 7-0 silk suture is used.

A surgeon passes the suture 60 into a surgical needle as in the example shown in FIG. 13(A), passes the surgical needle in such a manner as to scoop up an upper half layer of the sclera 130 as shown in FIG. 14, and bridges the suture 60 over the stitching and engaging portions 35 to stitch the lens ring 30 on the eyeball 100.

The example shown in FIG. 13(B) is a stitching method in a case in which the lens ring 30 is detachable.

The surgeon passes the suture 60 into the surgical needle, passes the surgical needle in such a manner as to scoop up the upper half layer of the sclera 130 as shown in FIG. 14 along the circumference of the lens ring 30 to fix the stitching and engaging portions 36 and 37, and finally ties a temporary knot 61 of the suture 60. When the lens ring 30 is detached, the temporary knot 61 is untied and the suture 60 is loosened to remove the suture from the stitching and engaging portions 36 and 37. When the lens ring 30 is stitched again, the suture 60 is bridged over the stitching and engaging portions 36 and 37 and then the temporary knot 61 is tied again to fix the stitching and engaging portions 36 and 37 so that the lens ring 30 is stitched in the desired position again.

When the stitching of the lens ring 30 on the eyeball 100 is completed in the above-described way, as shown in FIG. 12, the surgeon inserts a scalpel into the eyeball 100 and a light guide 80 for illuminating the surgical field, a vitreous body cutter 70 for cutting and sucking the vitreous body in the eyeball 100, an infusion 90 for injecting perfusate of an equivalent quantity to the quantity of the sucked vitreous body, and so on are inserted into the eyeball 100 to perform interocular surgery.

In FIG. 12, above the surgical lens 50, a not-shown surgical microscope is set and the surgeon performs the surgery while observing the surgical field through the surgical microscope and the surgical lens 50. If it is required to observe a different surgical field as the surgery progresses, the surgical lens 50 is appropriately rotated using a swab 75 or a fingertip and the like or replaced by the surgical lens 50 having a different shape, or the stitching position of the lens ring 30 is changed as described above.

It has been made to be clear by the inventors that, in the interocular surgery performed as described above, there are following problems.

To begin with, a first problem is that the passing the surgical needle in such a manner as to scoop up the upper half layer of the sclera 130 is an operation requiring the greatest care and time even for a skilled surgeon. Moreover, since this stage is a preparatory stage for the interocular surgery, imposing a burden of paying attention on the surgeon and consuming the time in this stage are greatly disadvantageous to the subsequent interocular surgery.

Further, a second problem is that, even if the skilled surgeon pays close attention, in case the surgical needle penetrates the sclera 130, tissues under the sclera are damaged, which may cause a complication after the surgery.

A third problem is that, even if the surgery needle does not penetrate the sclera 130, it is obvious that the surgical needle and the suture 60 are invasive for the sclera 130.

A fourth problem is that, since the lens ring 30 is fixed on the eyeball 100, every time when the lens ring 30 interferes with a surgical operation as the surgery progresses, the lens ring 30 is needed to be detached by cutting the suture 60 or by untying the temporary knot 61 to loosen the suture 60 and the first to third problems are repeated.

For example, in so-called triple surgery, in which three types of surgery, that is, ultrasonic surgery for emulsifying and sucking crystalline lens, retina and vitreous body surgery, and surgery for inserting an interocular lens are performed at the same time, the surgery progresses in the order of, for example, (イ) ultrasonic emulsification and suction of the crystalline lens, (ロ) vitreous body surgery, (ハ) interocular lens insertion, and (ニ) air displacement and interocular light solidification, and the surgical lens 50 is necessary in the stages of (ロ) and (ニ) while the surgery cannot be performed if the surgical lens 50 and the lens ring 30 are stitched on the eyeball 100 in the stage of (ハ). As a result, it is required to detach the lens ring 30 by cutting or loosening the suture 60 when the stage goes from (ロ) to (ハ) and to stitch the lens ring 30 again when the stage goes from (ハ) to (ニ).

A fifth problem is that, since the lens ring 30 is fixed on the eyeball 100, there is a part which cannot be observed even if the surgical lens 50 is rotated or replaced as described above.

In this case, conventionally, the surgical lens 50 is slightly tilted in the lens ring 30 to perform observation, but it is difficult to finely adjust the tilt.

As a result of dedicated study in order to solve the aforesaid problems, the inventors have thought that the problems can be solved all at once if the lens ring 30 is connected to the eyelid openers 10, not to the eyeball 100.

DISCLOSURE OF THE INVENTION

More specifically, a first invention is a holding apparatus for a vitreous body surgical contact lens, which is characterized in that it comprises: eyelid opener portions for pulling and opening an upper eyelid and a lower eyelid; a holding portion for holding the vitreous body surgical contact lens on an eyeball; and a connecting poring for connecting the eyelid opener portions with the holding portion for the vitreous body surgical contact lens, in which the vitreous body surgical contact lens is held on the eyeball.

A second invention is the holding apparatus for the vitreous body surgical contact lens according to the first invention, which is characterized in that the holding portion for the vitreous body surgical contact lens is connected with the eyelid opener portions in a manner in which a position thereof is adjustable.

A third invention is the holding apparatus for the vitreous body surgical contact lens according to either the first or second invention, which is characterized in that the eyelid opener portions have a structure in which a portion pulling the upper eyelid and a portion pulling the lower eyelid are integrated with an elastic portion therebetween.

A fourth invention is the holding apparatus for the vitreous body surgical contact lens according to any one of the first to third inventions, which is characterized in that the holding portion for the vitreous body surgical contact lens has a shape of a ring.

A fifth invention is the holding apparatus for the vitreous body surgical contact lens according to any one of the first to fourth inventions, which is characterized in that the connecting portion is composed of an elastic member.

A sixth invention is the holding apparatus for the vitreous body surgical contact lens according to claim 5, which is characterized in that the elastic member is a cord body.

A seventh invention is the holding apparatus for vitreous body surgical contact lens according to either the fifth or sixth invention, which is characterized in that the elastic member is silicone rubber.

An eighth invention is the holding apparatus for the vitreous body surgical contact lens according to any one of claims 1 to 7, which is characterized in that the holding portion for the vitreous body surgical contact lens has an engaging portion to be hooked by the connecting portion, and that the connecting portion has a hole to be engaged with the engaging portion.

A ninth invention is the holding portion used for the holding apparatus for the vitreous body surgical contact lens according to any one of the first to eight inventions, which is characterized in that it comprises the engaging portion in at least two positions, in which the holding portion is used by connecting with the eyelid opener portions via the connecting portion which is hooked on the engaging portion.

The tenth invention is the holding portion for the vitreous body surgical contact lens according to the ninth invention, which is characterized in that a lower inner circumferential surface of a cylindrical body portion forming the holding portion for the vitreous body surgical contact lens is chamfered following a shape of the eyeball.

An eleventh invention is the holding portion for the vitreous body surgical contact lens according to either the ninth or tenth invention, which is characterized in that a surface of the cylindrical body portion forming the holding portion for the vitreous body surgical contact lens is frosted.

A twelfth invention is the connecting portion used for the holding apparatus for the vitreous body surgical contact lens according to any one of the first to eighth inventions, which is characterized in that it comprises: a closed loop member for connecting the holding portion for the vitreous body surgical contact lens having elasticity and being capable of connecting the holding portion for the vitreous body surgical contact lens in a semi-fixed state with friction.

A thirteenth invention is the connecting portion according to the twelfth invention, which is characterized in that the closed loop member for connecting the holding portion for the vitreous body surgical contact lens having elasticity and being capable of connecting the holding portion for the vitreous body surgical contact lens in the semi-fixed state with friction is a rubber member having a ring shape.

A fourteenth invention is the connecting portion according to either of the twelfth or thirteenth invention, which is characterized in that at least one or more engaging holes for engaging with engaging portion of the holding portion for the vitreous body surgical contact lens are provided in the closed loop member having the ring shape.

A fifteenth invention is the connecting portion according to either of the twelfth or thirteenth invention, which is characterized in that a substantially rectangular engaging hole is provided in the closed loop member having the ring shape.

BEST MODE FOR CARRYING OUT THE INVENTION

Embodiments of the present invention will be detailed below with reference to the drawings.

Figure 1:
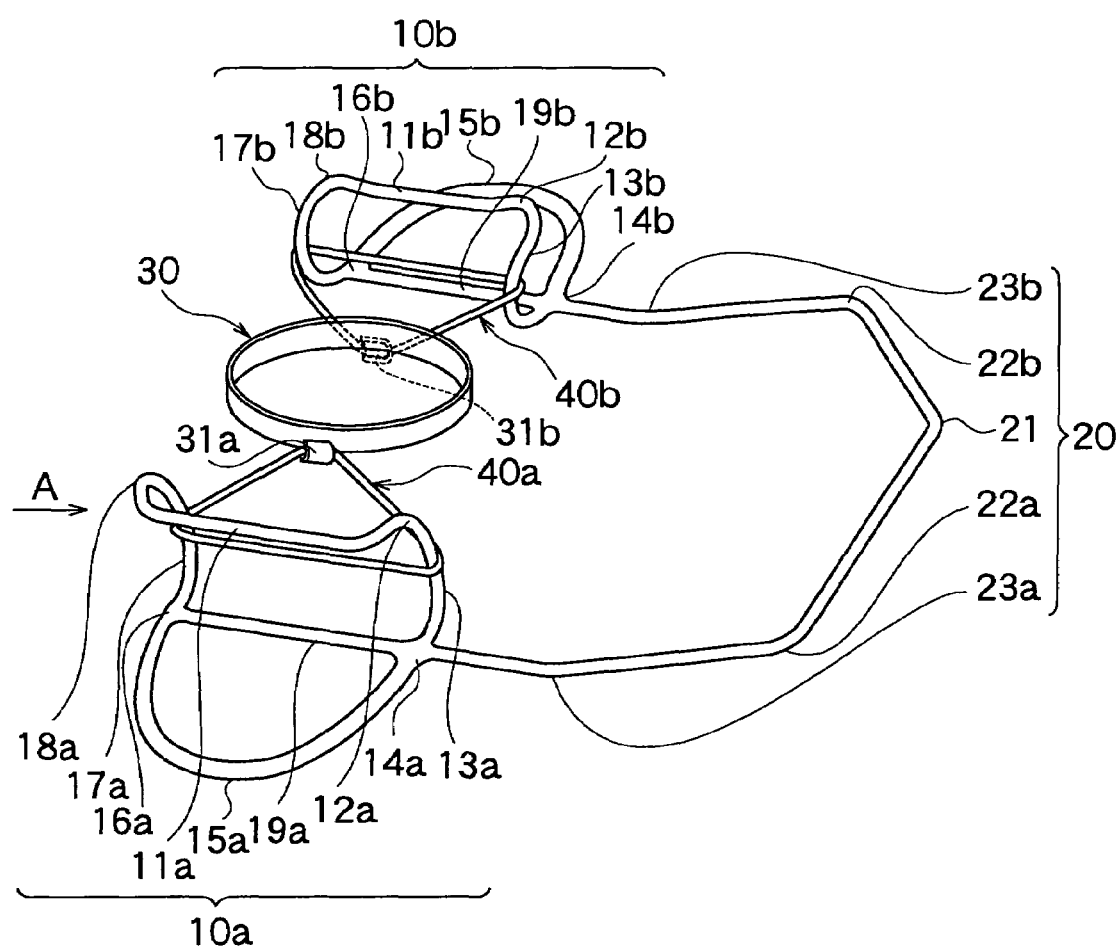
FIG. 1 is a perspective view of a holding apparatus according to an embodiment of the present invention seen in a state in which the apparatus in practical use is turned over.

FIG. 1 is a perspective view of a holding apparatus 1 for a vitreous body surgical contact lens (hereinafter referred to as holding apparatus 1) according to the embodiment of the present invention seen in a state in which the apparatus in practical use is turned over.

The holding apparatus 1 includes a pair of eyelid opener portions 10a and 10b for pulling and opening an upper eyelid and a lower eyelid of a human body, a spring portion 20 for supporting the pair of eyelid opener portions 10a and 10b, a pair of connecting portions 40a and 40b for connecting the eyelid opener portions 10a and 10b and a lens ring 30, and the lens ring 30 which is a holding portion for holding the surgical lens on an eyeball.

Each part of the holding apparatus 1 will be explained in detail now.

First of all, the pair of eyelid opener portions 10a and 10b will be explained taking the eyelid opener portion 10a as an example with reference to FIG. 1. Incidentally, the explanation can also be applied to the eyelid opener portion 10b.

The eyelid opener portion 10a is formed in a manner in which a bar whose cross section is substantially a round shape or an elliptic shape or a chamfered square bar is made to be a closed loop having substantially a semi-elliptic shape without acute angle portions and thereafter it is gently bent so that the straight line and the curved line thereof face each other to have a shape of substantially a letter "J" when seen from an arrow A, in which an inserting portion 11a which is the straight line, traction portions 13a and 17a which are two bent parts, and a supporting portion 15a which is the curved line are formed.

A bent portion 12a exists between the inserting portion 11a and the traction portion 13a, and a bent portion 18a exists between the inserting portion 11a and the traction portion 17a so that the inserting portion 11a inserted under the eyelid of a patient can obtain sufficient holding power without damaging tissues of a human body. The gentle bent of the traction portions 13a and 17a is provided for the same purpose and no acute angle part exists in these portions.

Further, between portions 14a and 16a, which are boundary parts between the traction portions 13a and 17a which are the bent parts and the supporting portion 15a which is the curved line, a bar 19a having a cross section of a substantially round shape or a substantially elliptic shape is bridged, and a part having an arcuate shape composed of the boundary part 14a, the supporting portion 15a, the boundary part 16a, and the bar 19a is in close contact with a face of the patient to support the holding apparatus 1.

The other eyelid opener portion 10b of the pair of eyelid opener portions 10a and 10b also has portions 11b to 19b which are symmetrical to the portions 11a to 19a of the eyelid opener portion 10a.

Next, the spring portion 20 will be explained with reference to FIG. 1.

The spring portion 20 is integrated with the bar 19a explained with the eyelid opener portions 10a and 10b, and then integrated with the bar 19b via bent portions 23a, 22a, 21, 22b, and 23b to support the eyelid opener portions 10a and 10b with elasticity. This part may have a simple U letter shape but, in this embodiment, a preferable structure in which a finger of a surgeon does not slip easily in opening and closing is employed by providing the bent portions 22a, 21, and 22b.

Moreover, the structure is also preferable in that, by bending the spring portion 20 upward in FIG. 1 by the bent portions 23a and 23b, the entire spring portion 20 including the bent portions 23a, 22a, 21, 22b, and 23b can become in close contact with the face of the patient when the holding apparatus 1 is set on the patient.

Subsequently, the lens ring 30 which is the holding portion for holding the surgical lens on the eyeball and the pair of connecting portions 40a and 40b will be explained with reference to FIG. 1. Incidentally, the pair of connecting portions 40a and 40b are the same portions and the connecting portion 40a will be explained as an example.

The lens ring 30 has a cylindrical body with its upper and lower faces being open and within which the later-described surgical lens is mounted. It includes, as described above, two or more (an example of two is shown in FIG. 1) engaging portions 31a and 31b (hereinafter shortened as engaging portions 31 in some cases) on its outer side face.

The connecting portion 40a is a closed loop member having elasticity and bridged between the traction portions 13a and 17a provided in the eyelid opener portion 10a and the engaging portion 31a provided on the lens ring 30 and whose cross section is an arcuate shape, to connect the lens ring 30 between the eyelid opener portions 10a and 10b in a semi-fixed state.

Next, the holding apparatus 1 will be further explained with reference to FIG. 2.

Figure 2:
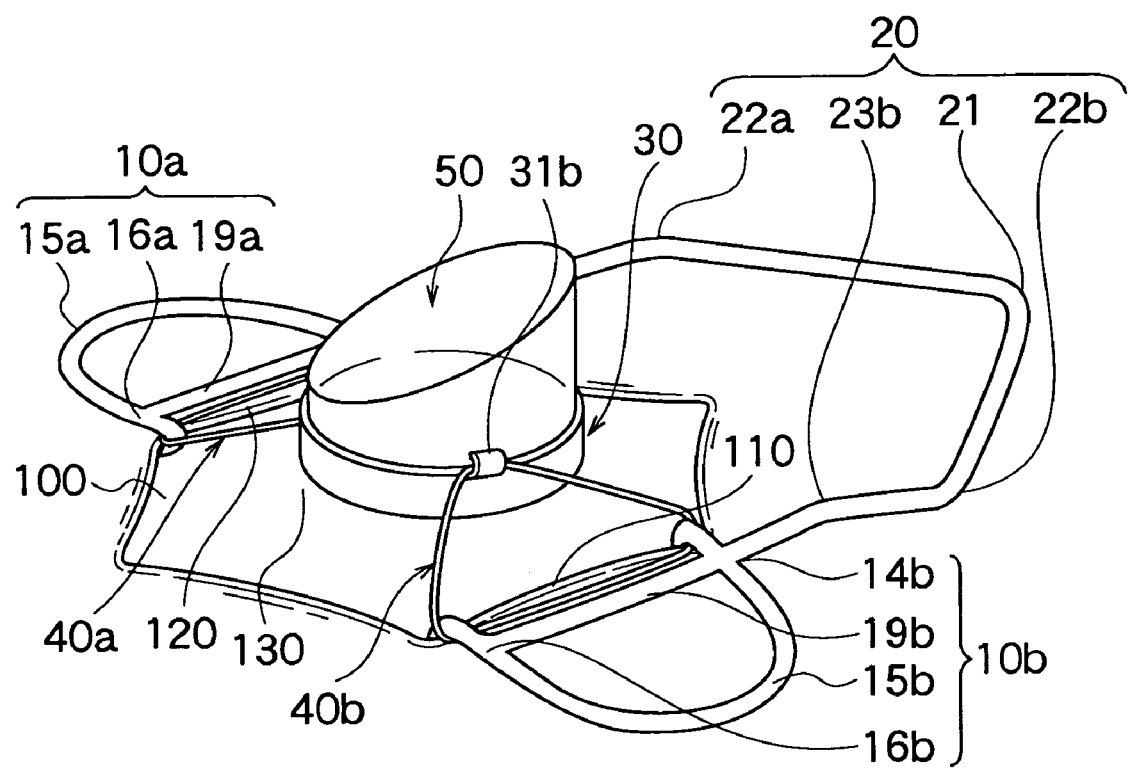
FIG. 2 is a perspective view showing a state in which the holding apparatus according to the embodiment of the present invention is set on an eyeball of a patient.

FIG. 2 is a perspective view showing a state in which the surgical lens is mounted in the holding apparatus and held on a cornea of the eyeball of the patient.

In FIG. 2, the holding apparatus 1 is set on an eyeball 100 of the patient.

At this time, the inserting portions 11a and 11b and the traction portions 13a, 13b, 17a, and 17b of the pair of eyelid opener portions 10a and 10b, which are inserted under upper and lower eyelids 110 and 120 of the patient and not shown in the drawing, open the upper eyelid 110 and the lower eyelid 120 by pulling them with appropriate power by the elasticity of the spring portion 20.

Meanwhile, the supporting portions 15a and 15b, the bars 19a and 19b, and the spring portion 20 are in close contact with the face of the patient to support the eyelid opener portions 10a and 10b.

At this time, the pair of connecting portions 40a and 40b connect the eyelid opener portion 10a with the engaging portion 31a of the lens ring 30, and the eyelid opener portion 10b with the engaging portion 31b of the lens ring 30 with appropriate tension. As a result, a surgical lens 50 mounted in the lens ring 30 is semi-fixed in a desired position such as, for example, a position immediately above the cornea in the eyeball 100 of the patient.

This method has significant advantages such as easiness which reduces the burden on the surgeon and harmlessness to the tissues of the human body of the patient.

As a mechanism for supporting the pair of eyelid opener portions 10a and 10b, mechanical mechanisms such as a mechanism in which a screw and a spring are combined, a mechanism in which a male thread and a female thread are combined, a mechanism in which a rack and a pinion are combined, or the like can be used other than the aforesaid method using the elasticity of the spring portion 20. It is also a preferable structure to precisely pulling the eyelids by the pair of eyelid opener portions 10a and 10b using these mechanisms.

As material of the eyelid opener portions 10a and 10b and the spring portion 20, metallic materials such as stainless steel, aluminum, titanium, iron, copper, silver, gold, platinum, or an alloy including aluminum, titanium, iron, copper, nickel, and so on, or resin materials, for example, methacrylic resins such as polymethyl methacrylate, a polycarbonate resin, fluorine resins such as polytetrafluoroethylene, a polyimide resin, and other variety of thermosetting and thermoplastic resins can be used.

Moreover, the spring portion 20 is required to have sufficient elasticity, to be harmless to the human body so as not to cause allergy, to be easy to sterilize, and so on, and considering the cost for the material, stainless steel, aluminum, titanium, and the like are preferable as the metallic material and polymethyl methacrylate and the like are preferable as the resin material.

Next, the lens ring according to the present invention will be further explained with reference to FIG. 3.

Figure 3A:
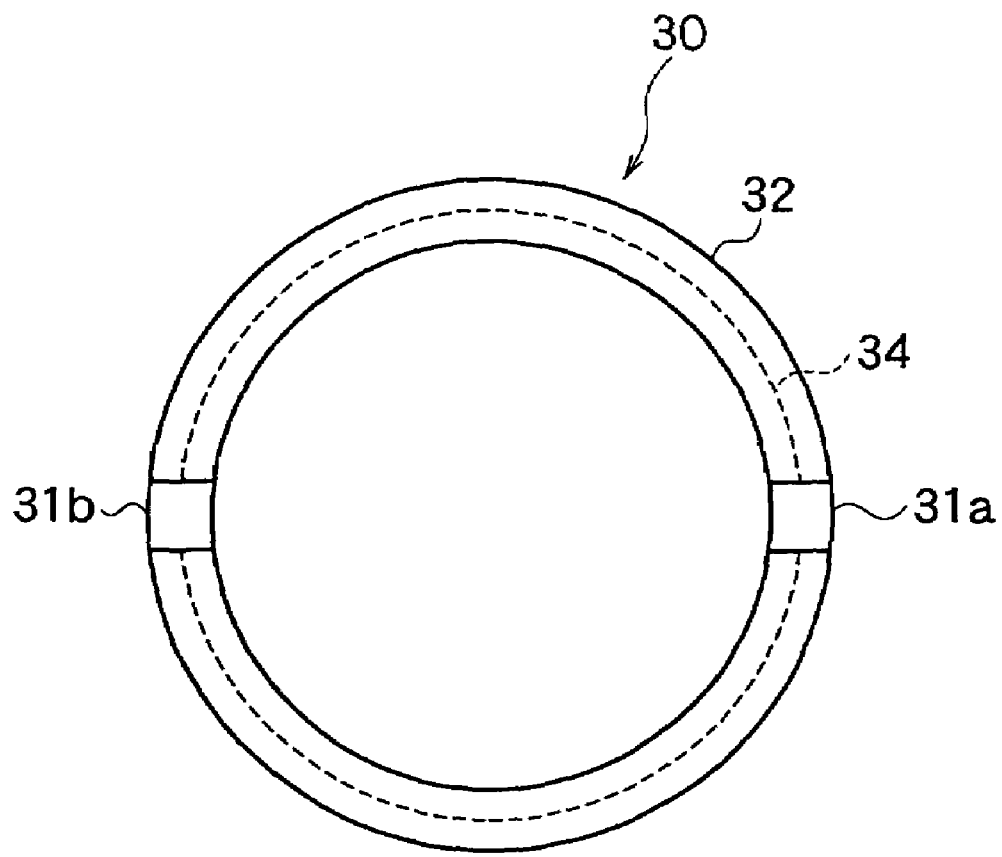
FIG. 3 is examples of a plan view and a side view of a lens ring according to the embodiment of the present invention.
Figure 3B:
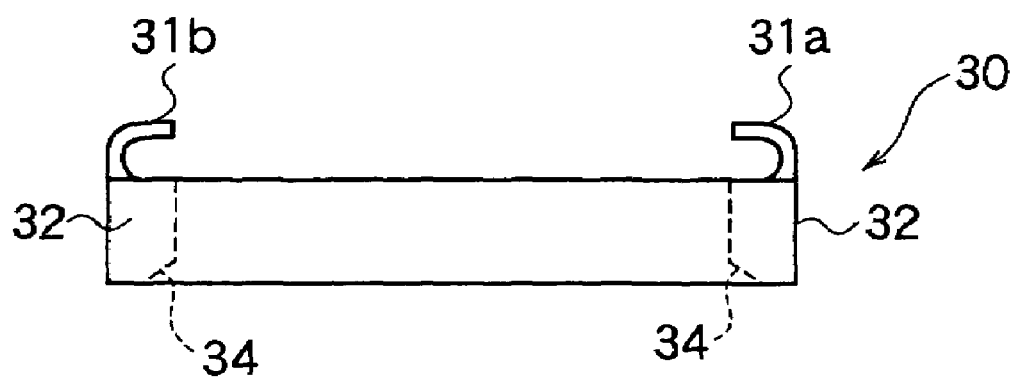

FIG. 3(A) is a plan view of the lens ring 30 and FIG. 3(B) is its side view.

The lens ring 30 is a cylindrical body with its upper and lower faces being open composed of a cylindrical body portion 32. On an upper surface of the cylindrical body portion 32, two or more (an example of two is shown in FIG. 3) engaging portions 31a and 31b having cross sections of the arcuate shape are provided with their curved surfaces facing inward. The lens ring 30 is connected with the traction portions 13a and 17a and traction portions 13b and 17b of the holding apparatus 1 by hooking the pair of connecting portions 40a and 40b on the engaging portions 31a and 31b, which is a preferable structure in which the connecting portions 40a and 40b are easily unhooked but not accidentally unhooked because the curved surfaces face inward.

In general, the positions where the engaging portions 31a and 31b are set in the lens ring 30 are preferably provided in upper parts or at side ends of the upper parts of the lens ring 30 which are not in contact with the eyeball 100 from a viewpoint of reducing a burden on the eyeball 100. However, it is also possible to provide the engaging portions 31a and 31b in lower parts or at ends of the lower parts of the lens ring 30 as long as consideration is given to the shape and the material of the engaging portions 31a and 31b, which is a preferable structure from a viewpoint of securely holding the surgical lens 50.

Further, the shape of the cross section of the lens ring 30 is not limited to the round shape and any shape is possible as long as it can hold the surgical lens 50 in the desired position. Thus, it is also a preferable structure to employ an elliptic shape or a polygonal shape such as a triangle, a rectangle, a pentagon, . . . according to the shape of the surgical lens 50 or the operability of the surgeon and so on.

Furthermore, it is also a preferable structure in which gentle chamfering 34 is provided on a lower inner circumferential surface of the cylindrical body portion 32 along a shape of the eyeball of the patient so as to reduce the burden on the eyeball of the patient.

Now different embodiments of the lens ring 30 and the engaging portions 31 will be explained with reference to FIG. 4 to FIG. 6.

Figure 4A:
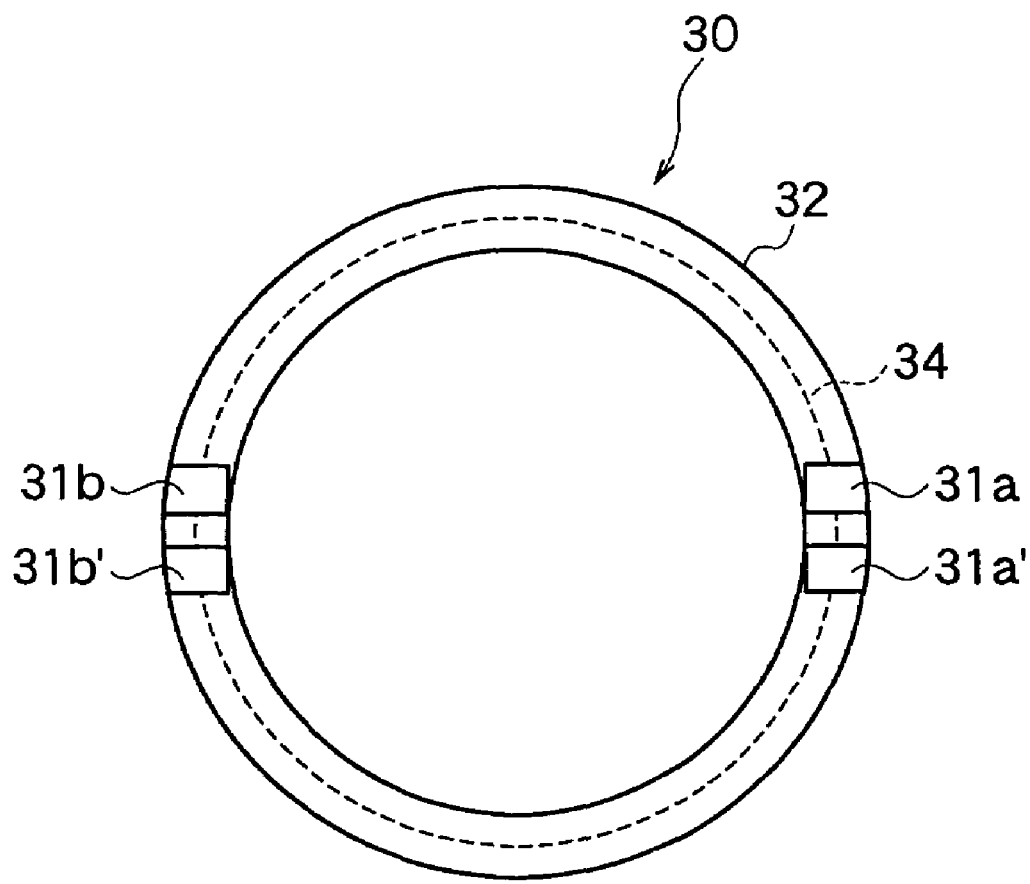
FIG. 4 is examples of a plan view and a side view of the lens ring according to another embodiment of the present invention.
Figure 4B:
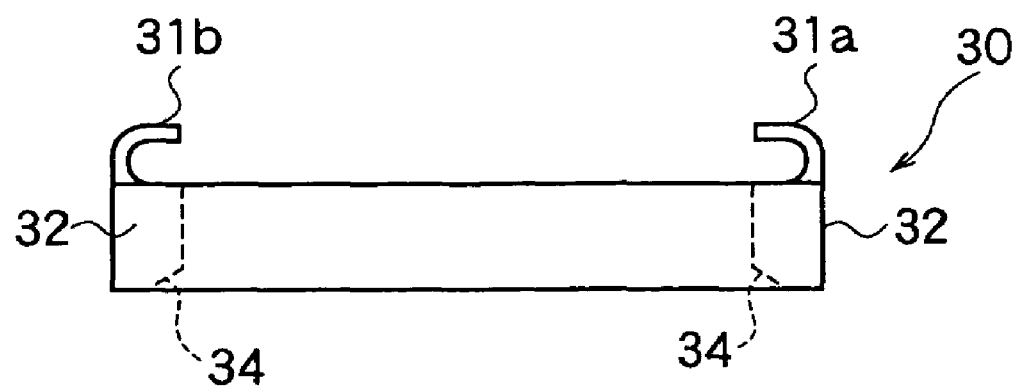
Figure 5A:
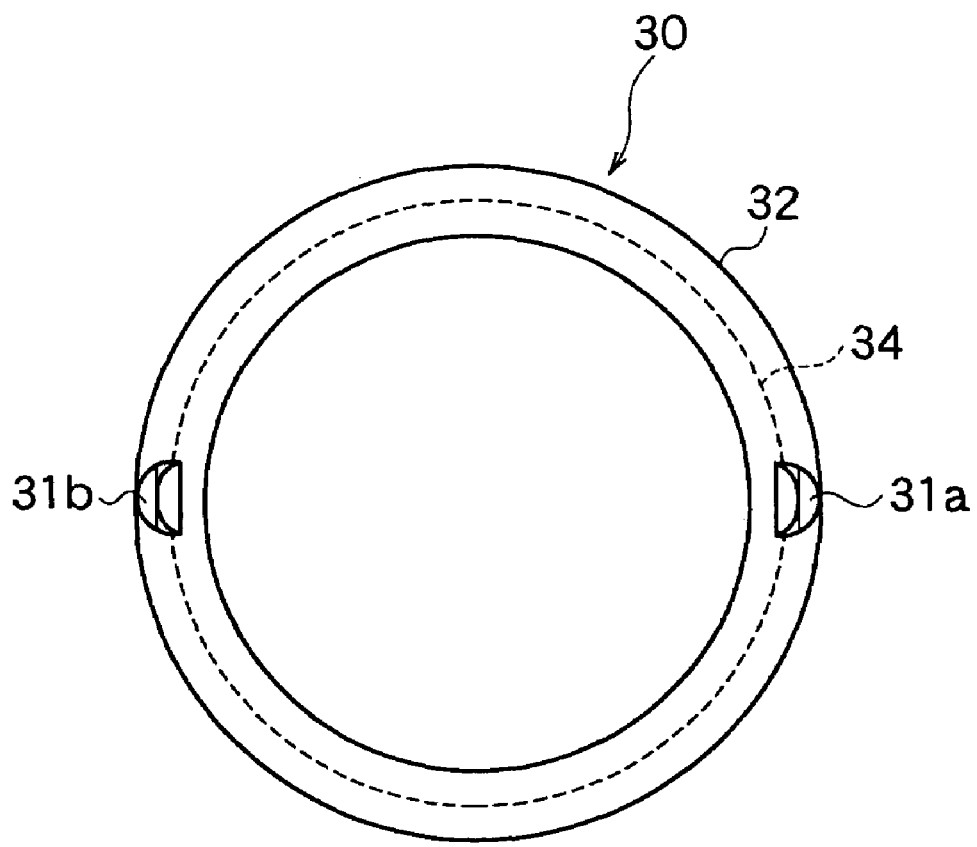
FIG. 5 is examples of a plan view and a side view of the lens ring according to still another embodiment of the present invention.
Figure 5B:
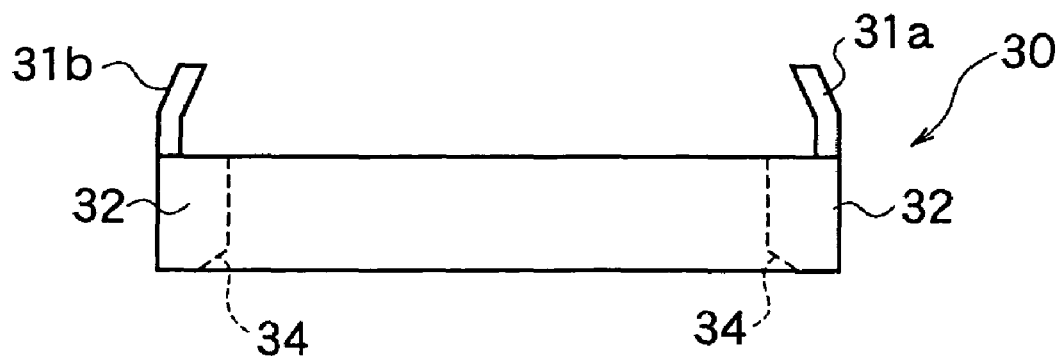
Figure 6A:
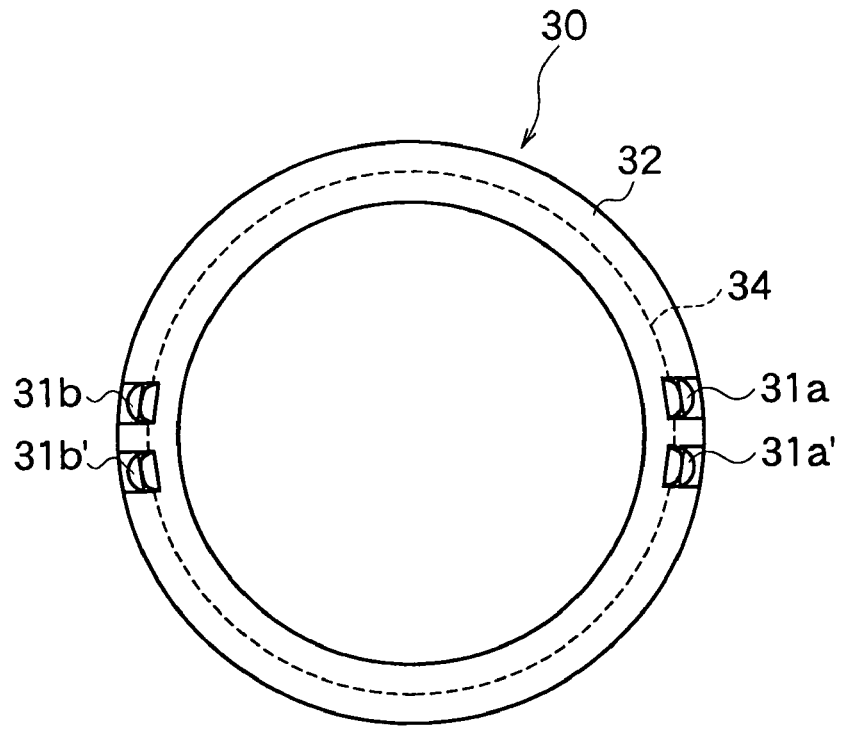
FIG. 6 is examples of a plan view and a side view of the lens ring according to yet another embodiment of the present invention.
Figure 6B:
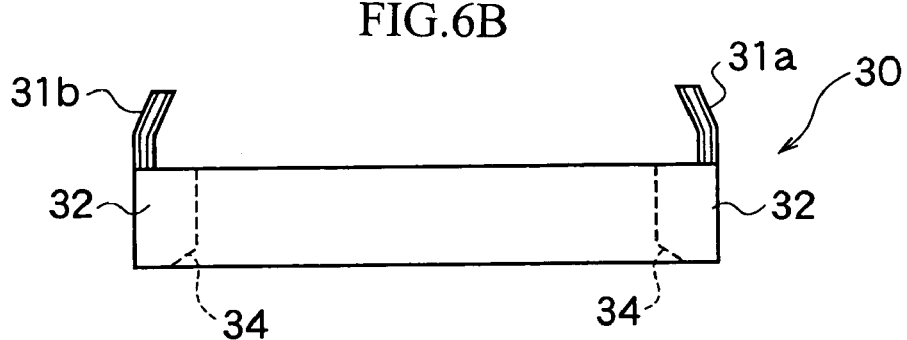

FIG. 4(A), FIG. 5(A), and FIG. 6(A) are plan views of the lens ring 30 and the engaging portions 31 according to the different embodiments and FIG. 4(B), FIG. 5(B), and FIG. 6(B) are their side views.

The lens ring 30 and the engaging portions 31 shown in FIG. 4 are examples in which the cross sections of the engaging portions 31a and 31b have the arcuate shape, similar to those in FIG. 3, but two engaging portions 31 are provided in each of positions facing each other on the upper surface of the cylindrical body portion 32, which indicates that four engaging portions 31 (engaging portions 31a, 31a', 31b, and 31b') are provided on the circumference of the lens ring 30.

As shown in FIG. 4, when the two engaging portions 31 are provided in each of the opposing positions, one of the connecting portions is hooked on the engaging portions 31a and 31a' while the other one of the connecting portions is hooked on the engaging portions 31b and 31b', which stabilizes the connection so that the lens ring 30 is dynamically stabled. Accordingly, it is a preferable structure for a case, for example, in which the position of the lens ring 30 is often moved on the eyeball, or the like, Also in this embodiment, it is a preferable structure in which the gentle chamfering 34 is provided on the lower inner circumferential surface of the cylindrical body portion 32 along the shape of the eyeball of the patient so as to reduce the burden on the eyeball of the patient.

The lens ring 30 and the engaging portions 31a and 31b shown in FIG. 5 are examples different from those in FIG. 3 in that the engaging portions 31a and 31b have the cross sections of a shape of a letter "V" and are provided in two opposing positions on the upper surface of the cylindrical body portion 32.

When the engaging portions 31a and 31b have the shape of the letter "V" as in this embodiment, the pair of connecting portions can be easily unhooked from the engaging portions 31a and 31b when necessary.

For example, when the lens ring 30 is mounted and detached multiple times during surgery such as the triple surgery, the connecting portions can be easily unhooked from the lens ring 30 if the engaging portions 31 have the shape of the letter "V", which is a preferable structure.

Also in this embodiment, it is also a preferable structure in which the gentle chamfering 34 is provided on the lower inner circumferential surface of the cylindrical body portion 32 of the lens ring 30 along the shape of the eyeball of the patient so as to reduce the burden on the eyeball of the patient.

The lens ring 30 and the engaging portions 31 shown in FIG. 6 are examples similar to those in FIG. 5 in that the cross sections of the engaging portions 31 have the shape of the letter "V", but different in that, while each one of the engaging portions 31 is provided in respective one of the opposing positions on the upper surface of the cylindrical body portion 32 in FIG. 5, two engaging portions 31 are provided in each of the positions facing each other, which indicates that four portions (the engaging portions 31a, 31a', 31b, and 31b') are provided on the circumference of the lens ring 30.

As shown in FIG. 6, if the two engaging portions 31 are provided in each of the positions facing each other, one of the connecting portions is hooked on the engaging portions 31a and 31a' while the other one of the connecting portions is hooked on the engaging portions 31b and 31b', which stabilizes the connection so that the lens ring 30 is dynamically stabled. Accordingly, it is a particularly preferable structure for a case, for example, when the position of the lens ring 30 is moved on the eyeball during the triple surgery, or the like.

Also in this embodiment, it is a preferable structure in which the gentle chamfering 34 is provided on the lower inner circumferential surface of the cylindrical body portion 32 of the lens ring 30 along the shape of the eyeball of the patient so as to reduce the burden on the eyeball of the patient.

As material of the lens ring 30, metallic materials such as stainless steel, aluminum, titanium, iron, copper, silver, gold, platinum, or an alloy including aluminum, titanium, iron, copper, nickel, and so on, or resin materials, for example, a methacrylic resin such as polymethyl methacrylate, a polycarbonate resin, fluorine resins such as polytetrafluoroethylene, a polyimide resin, and other variety of thermosetting and thermoplastic resins can be used.

Here, if a shiny material is used as the material of the lens ring 30, it may reflect illumination light to interfere with the observation through a microscope during the surgery. In this case, it is also a preferable structure to frost the material of the lens ring 30 using a sandblast and the like.

Further, since the stitching with the suture becomes unnecessary, not only the aforesaid hard materials but also soft materials capable of holding the surgical lens 50 in the desired position can be also employed as the material of the lens ring 30. It is also a preferable structure to use these soft materials which are expected to further reduce the burden on the patient.

According to the above description, as in the holding apparatus 1, the lens ring 30 is required to be harmless to the human body so as not to cause allergy, to be easy to sterilize, and so on, and considering the cost for the material, stainless steel, aluminum, titanium, and the like are preferable as the metallic material, polymethyl methacrilate, hydrous resins, soft resins, and the like are preferable as the resin material, and silicone rubber, fluorine rubber, and the like are preferable as a rubber material In addition, it is also a preferable structure in which the lens ring 30 is manufactured at a low cost by injection molding or the like using the resin materials or the rubber materials so as to be used as a disposable lens in the surgery.

Subsequently, the connecting portion according to the present invention will be further explained with reference to FIG. 7.

As described above, the connecting portion is the portion which connects the traction portions of the holding apparatus and the engaging portion of the lens ring with elasticity.

The reason is that the connecting portion is required to have a function of adjusting a position and a function of holding the position in order to hold the surgical lens mounted in the lens ring in an optimal position on the eyeball since, in the body, there are variations of the size, shape, elasticity, and so on of the upper and lower eyelids and the eyeballs among patients to some extent and that, if the position of the lens can be slightly moved during the surgery, the observable area in the eyeball of the patient enlarges, which may enable further reduction in the burden on the surgeon.

Figure 7:
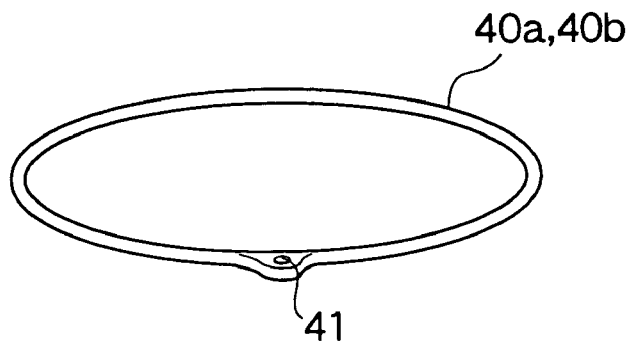
FIG. 7 is a perspective view showing an example of a connecting portion according to the embodiment of the present invention.

FIG. 7 is a perspective view of an example of a closed loop which is not a simple closed loop made of an elastic material but a closed loop a part of which has an engaging hole 41 as either of the pair of connecting portions 40a and 40b according to the embodiment of the present invention. Incidentally, both of the pair of connecting portions 40a and 40b have the same shape.

The material with the engaging hole is made to be the pair of connecting portions 40a and 40b and used in combination with the engaging portions 31 whose cross sections have the arcuate shape shown in FIG. 3 or the engaging portions 31 whose cross sections have the shape of the letter "V" shown in FIG. 5 described above, which realizes a preferable structure in which the pair of connecting portions 40a and 40b are not easily unhooked due to friction between the pair of connecting portions 40a and 40b and the engaging portions 31 even when unexpected force is given while they can be easily unhooked when they are wished to be unhooked.

Moreover, the structure is greatly advantageous in that the lens ring 30 is stabled because the connection between the engaging portions 31 and the pair of connecting portions 40a and 40b is fixed by the engaging holes 41, and so on.

Referring to FIG. 7 again, shown is an example in which one engaging hole 41 is provided in each closed loop of the connecting portions 40a and 40b, but it is preferable to provide the appropriate number of the holes in accordance with the structure of the engaging portions 31. Specifically, in the case of the aforesaid lens ring shown in FIG. 4 and FIG. 6, each closed loop of the connecting portions 40a and 40b is hooked on the two or more engaging portions 31 respectively, and at this time, it is preferable to make a structure in which a plurality of the engaging holes 41 are provided in each of the connecting portions 40a and 40b corresponding to the number of the engaging portions 31 and intervals therebetween.

As an example of the connecting portion according to the embodiment of the present invention, various forms other than the above-described connecting portions 40a and 40b shown in FIG. 7 can be naturally considered.

For example, the connecting portions 40a and 40b may be formed in a manner in which materials having a cord shape are tied to be closed loops and it is further preferable if the material having the cord shape is material with elasticity, for example, rubber. Since this structure can greatly reduce the cost of the connecting portions 40a and 40b, it is a preferable structure when the portions are made to be disposable.

Further, as a different form of the connecting portion, a plate shape may be employed instead of the cord shape and the material may be resin or metal instead of rubber. Furthermore, a spring member made of resin or metal may be used. Additionally, it is also a preferable structure to precisely adjust the position using a generally-known mechanical mechanism such as the mechanism using the male thread and the female thread, the mechanism using the rack and the pinion, or the like.

As material of the connecting portion, rubber materials such as silicone rubber, fluorine rubber, natural rubber, SBR, IR, butyl rubber, and neoprene rubber, or resin materials, for example, a methacrylic resin such as polymethyl methacrylate, a polycarbonate resin, fluorine resins such as polytetrafluoroethylene, a polyimide resin, and other variety of thermosetting and thermoplastic resins, or suture materials such as a silk suture, or metallic materials such as stainless steel, aluminum, titanium, iron, copper, silver, gold, platinum, or an alloy including aluminum, titanium, iron, copper, nickel or the like, and so on can be used.

Moreover, as in the eyelid opener portions 10 and the lens ring 30, the connecting portion is required to be harmless to the human body so as not to cause allergy, to be easy to sterilize, and so on, and considering the cost for the material, silicone rubber, fluorine rubber, and the like are preferable as the rubber material, stainless steel, aluminum, titanium, and the like are preferable as the metallic material, and polymethyl methacrylate and the like are preferable as the resin material.

In addition, it is also a preferable structure in which the pair of connecting portions 40a and 40b are manufactured at a low cost by injection molding or the like using the resin materials or the rubber materials so as to be used as disposable portions in the surgery.

Here an effect that the lens ring 30 and the connecting portions 40a and 40b according to the present invention reduce the burden on the eyeball of the patient in the vitreous body surgery will be further explained with reference to FIG. 8 and FIG. 9.

Figure 8:
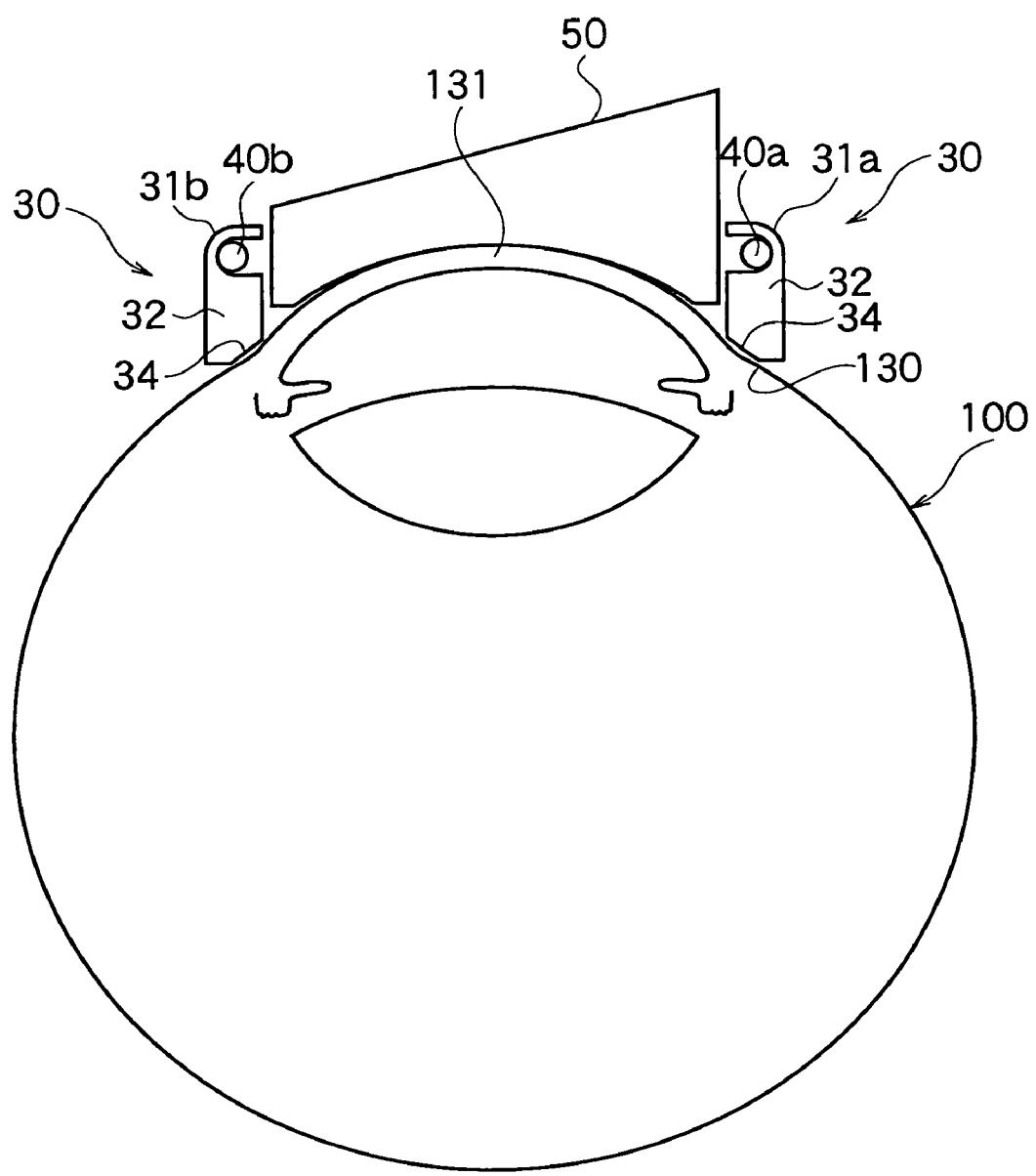
FIG. 8 is a cross-sectional view showing a state in which the holding apparatus according to the embodiment of the present invention is set on the eyeball of the patient.
Figure 9:
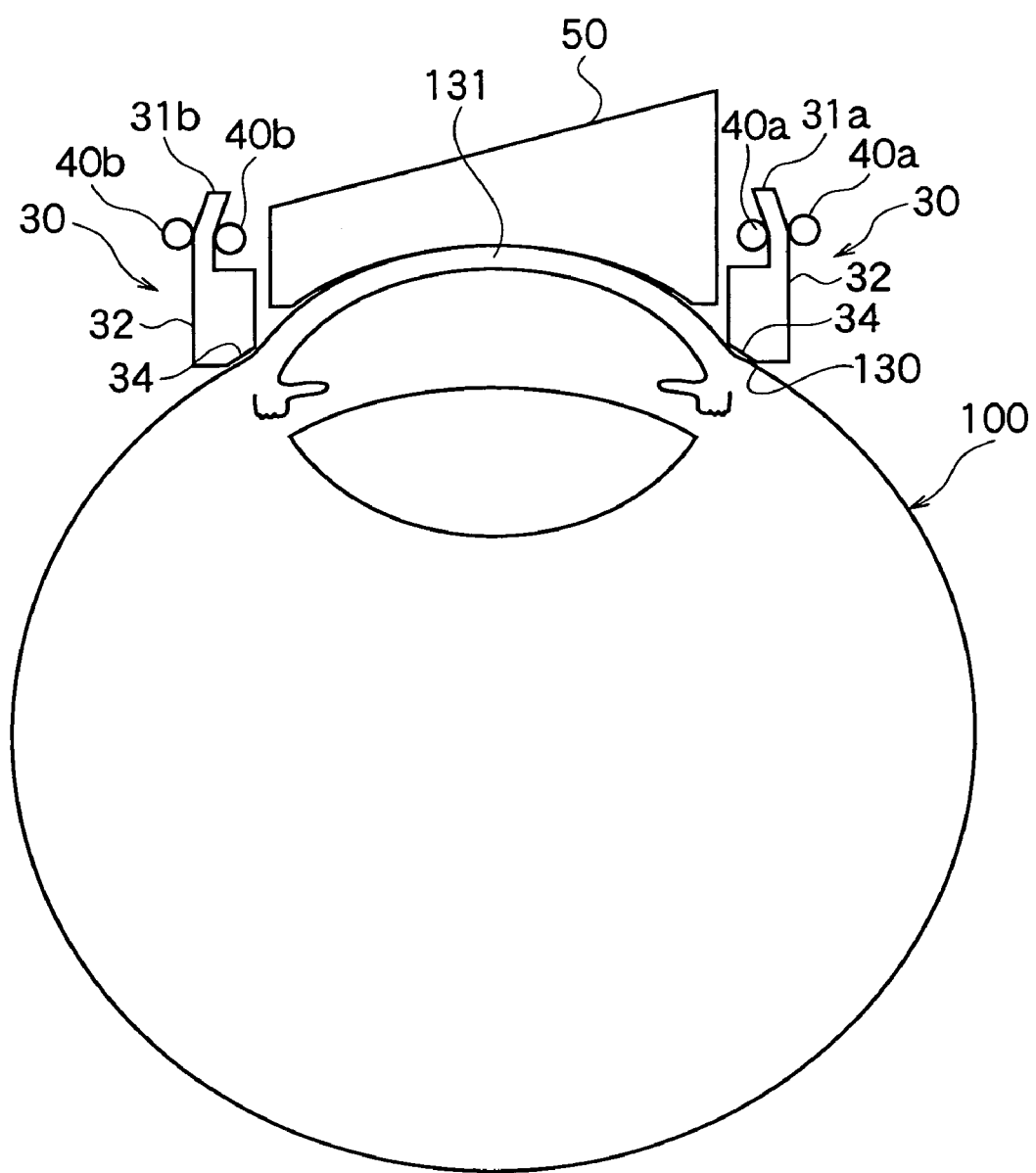
FIG. 9 is a cross-sectional view showing a state in which the holding apparatus according to another embodiment of the present invention is set on the eyeball of the patient.

FIG. 8 and FIG. 9 are cross-sectional views showing a state in which the surgical lens 50 is mounted within the aforesaid lens ring 30 and held on the sclera 130 of the eyeball 100 of the patient and FIG. 8 is an example of the lens ring 30 whose engaging portions 31 have the arcuate shape while FIG. 9 is an example of the lens ring 30 whose engaging portions 31 have the shape of the letter "V".

First, in FIG. 8, the chamfered surface 34 of the cylindrical body portion 32 of the lens ring 30 is in contact with the sclera 130 of the eyeball 100 of the patient. The lens ring 30 is connected with the not-shown eyelid opener portions 10a and 10b by the connecting portions 40a and 40b, which are respectively hooked on the engaging portions 31a and 31b having the arcuate shape, and semi-fixed in the desired position on the eyeball 100. The surgical lens 50 is mounted within the lens ring 30 which is semi-fixed in the desired position on the eyeball 100.

Next, in FIG. 9, the chamfered surface 34 of the cylindrical body portion 32 of the lens ring 30 is in contact with the sclera 130 of the eyeball 100 of the patient, as in FIG. 8. The connecting portions 40a and 40b having the engaging holes 41 are respectively hooked on the engaging portions 31a and 31b of the lens ring 30, which have the shape of the letter "V", so that the circumference of each of the engaging portions 31a and 31b having the shape of the letter "V" is in contact with the connecting portion 40a or 40b to obtain sufficient friction.

As a result, the lens ring 30 is connected with the not-shown eyelid opener portions 10a and 10b with sufficient stability. Meanwhile, when required, the connecting portions 40a and 40b can also be easily unhooked from the engaging portions 31a and 31b having the shape of the letter "V". As in FIG. 8, the surgical lens 50 is mounted within the lens ring 30 which is semi-fixed in the desired position on the eyeball 100.

In both of the examples in FIG. 8 and FIG. 9, it becomes possible to semi-fix the surgical lens 50 on a cornea 131 without stitching the lens ring 30 on the sclera 130, which brings about a large effect that the burden on the surgeon can be greatly reduced as well as the burden on the sclera 130 of the patient due to the surgical needle and the suture is removed.

Figure 13:
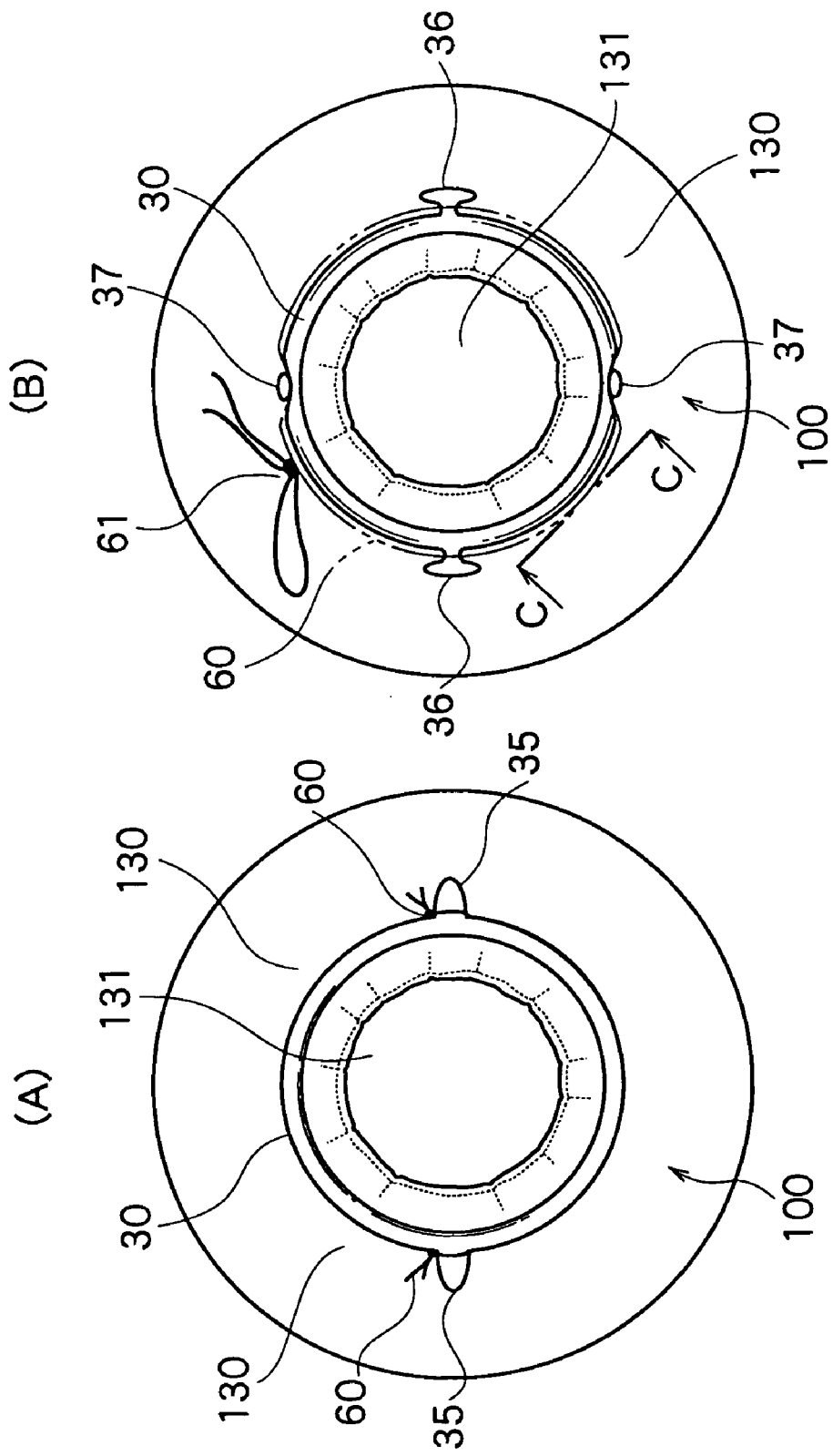
FIG. 13 is a plan view when the holding apparatus in the conventional art is set on the eyeball of the patient.
Figure 14:
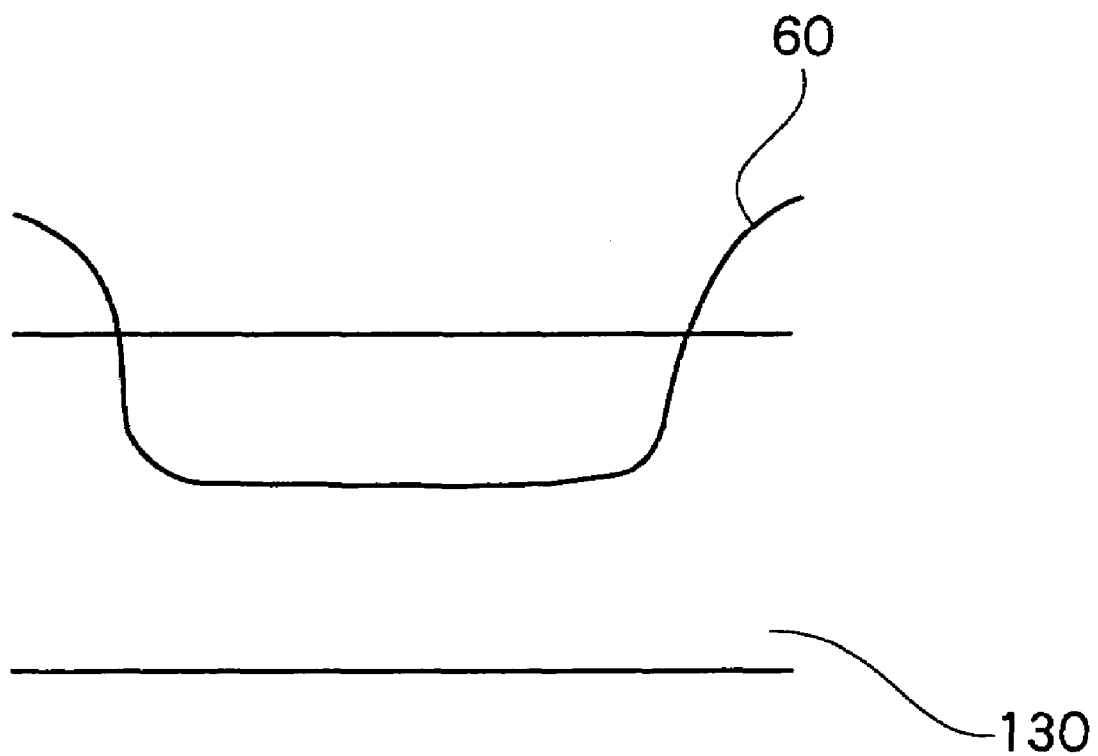
FIG. 14 is a cross-sectional view taken along the C-C line in FIG. 13.

More preferably, the stitching and engaging portion required in the conventional lens ring 30 explained in FIG. 13 becomes unnecessary, which makes it possible to gently provide the chamfering 34 on the entire lower inner circumferential surface of the cylindrical body portion 32 along the shape of the eyeball 100 so as to further reduce the burden on the sclera 130.

Figure 10:
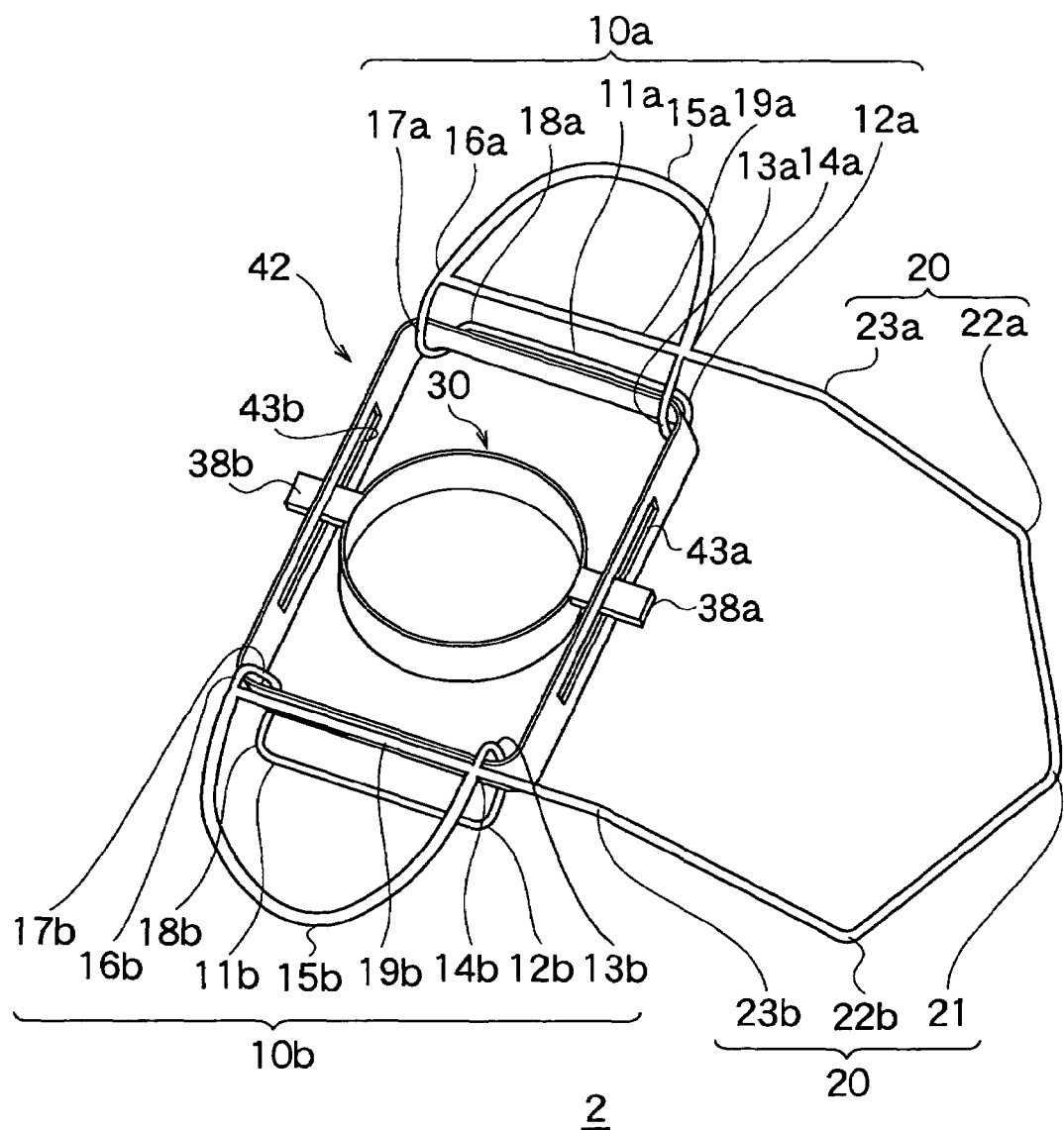
FIG. 10 is a perspective view of the holding apparatus according to the embodiment of the present invention, which has another form.
Figure 11:
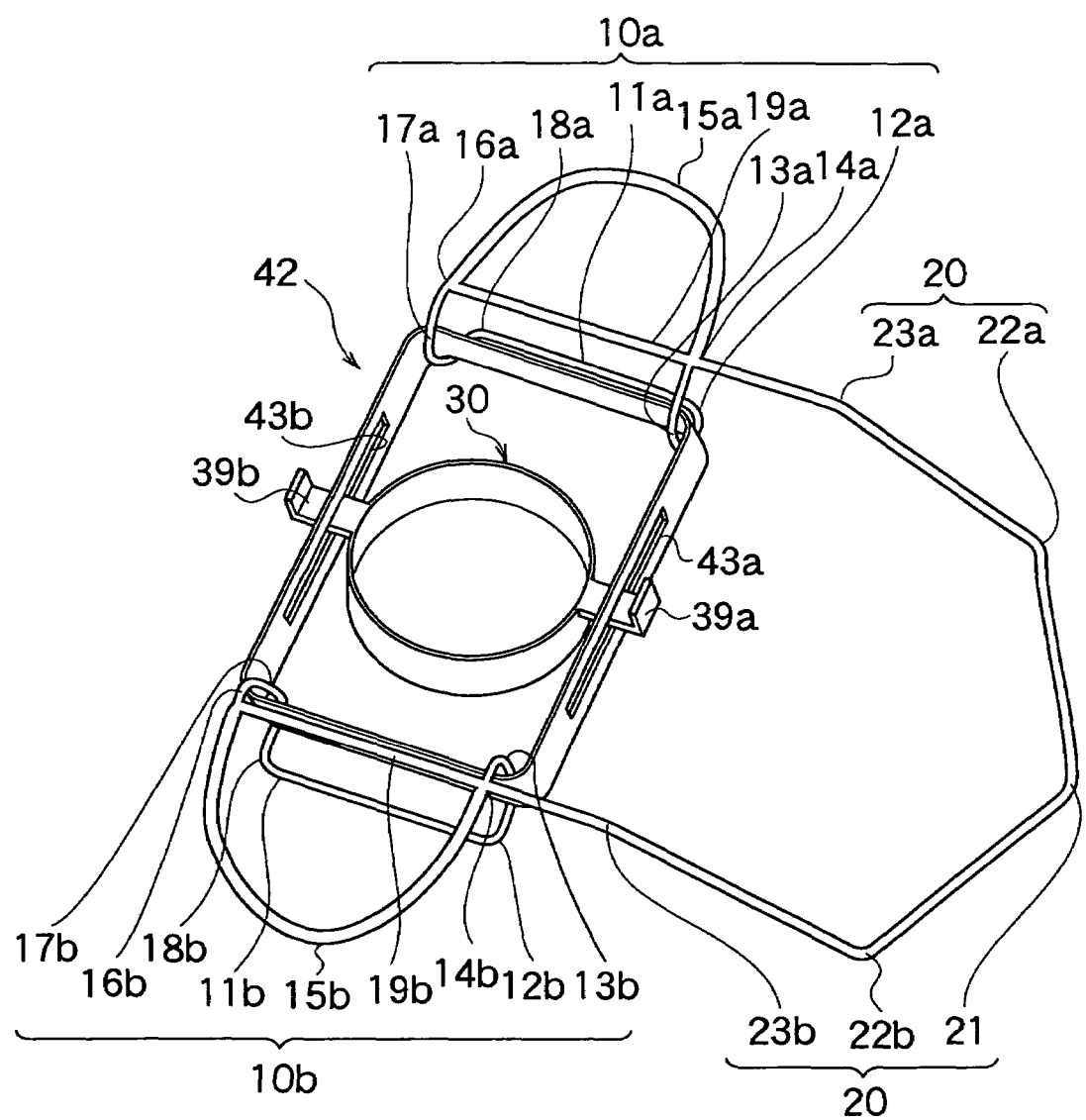
FIG. 11 is a perspective view of the holding apparatus according to the embodiment of the present invention, which has still another form.
Figure 12:
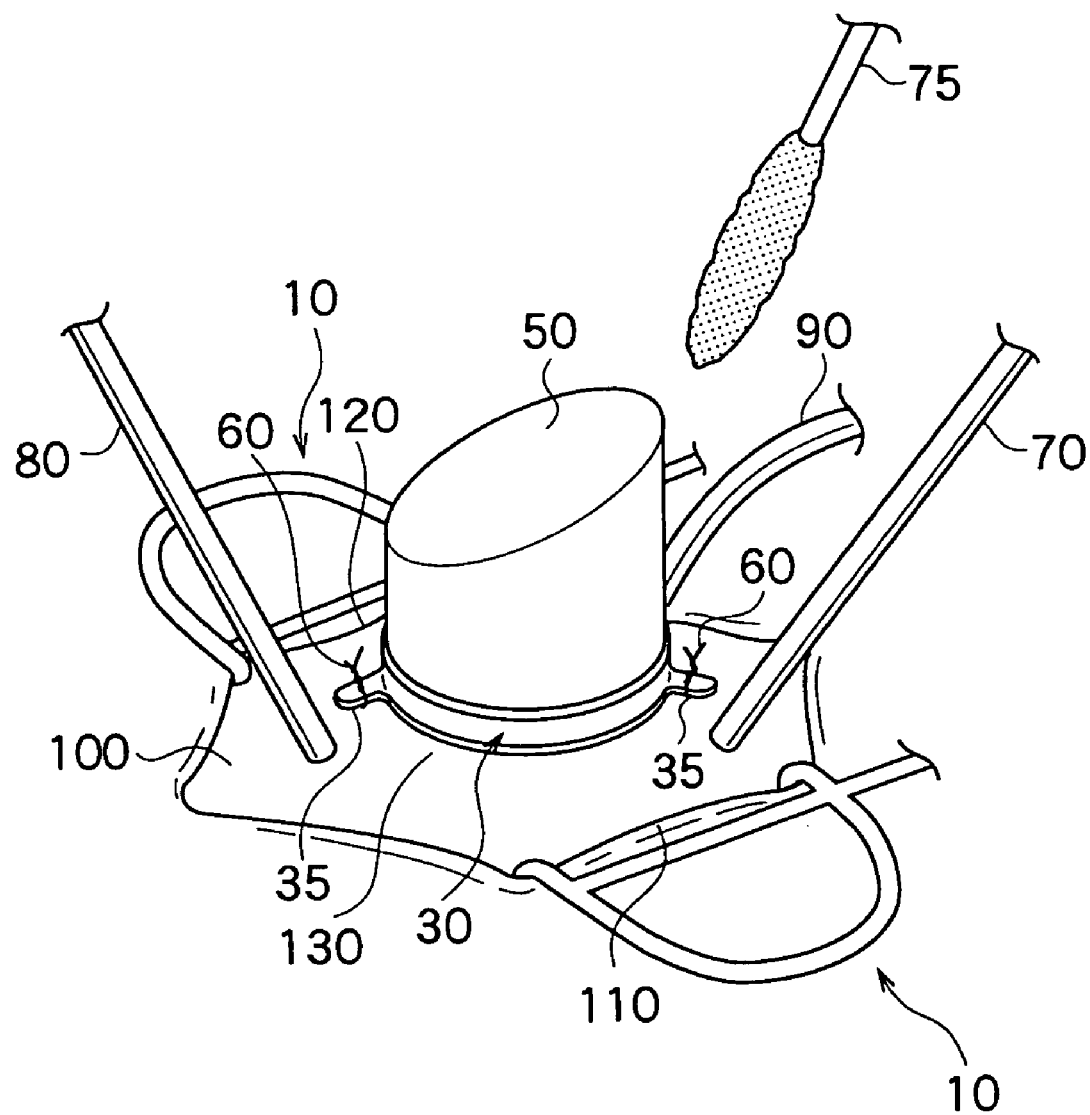
FIG. 12 is a perspective view showing a state in which a holding apparatus in a conventional art is set on the eyeball of the patient to perform vitreous body surgery.

FIG. 10 and FIG. 11 are perspective views of two kinds of holding apparatuses 2 and 3 for the vitreous body surgical contact lens according to still other embodiments of the present invention, seen from an upper part.

First, an example of the holding apparatus 2 for the vitreous body surgical contact lens will be explained with reference to FIG. 10.

In the holding apparatus 2, the same pair of eyelid opener portions 10a and 10b and spring portion 20 as those of the aforesaid holding apparatus 1 can be used.

Next, the lens ring 30 will be explained.

Though the engaging portions 31 described in the description of the holding apparatus 1 have the arcuate shape or the shape of the letter "V", a pair of engaging portions 38a and 38b included in the lens ring 30 are flat-shaped and project in diametrical directions from side faces of the lens ring 30 so as to be engaged with engaging holes provided in a later-described connecting portion 42.

As thus structured, the lens ring 30 can be easily set in the desired position on the eyeball.

More specifically, the flat-shaped engaging portions 38a and 38b of the lens ring 30 and horizontal engaging holes 43a and 43b provided in the later-described engaging portion 42 are engaged with each other with appropriate friction so that the lens ring 30 can be moved to any position on the eyeball within a range of allowance formed by the longitude of the engaging holes 43a and 43b, the flat-shaped engaging portions 38a and 38b, and the connecting portion 42 when the surgeon gives force on the lens ring 30. When the surgeon stops giving the force afterward, the lens ring 30 is stably semi-fixed by the aforesaid friction.

Incidentally, a structure may be also preferably employed in which the shape of the flat-shaped engaging portions 38a and 38b is a triangular shape, a cylindrical shape, or the like other than the rectangular shape shown in FIG. 10 to realize the dynamic stability of the lens ring 30.

Subsequently, the connecting portion 42 will be explained.

In FIG. 10, the connecting portion 42 is provided in a manner of bridging the traction portions 13a, 17a, 17b, and 13b of the pair of eyelid opener portions 10a and 10b. In the bridging part, the engaging holes 43a and 43b with which the above-described flat-shaped engaging portions 38a and 38b are engaged are provided between the traction portions 13a and 13b and between the traction portions 17a and 17b.

The width of the engaging holes 43a and 43b can be set as the width from which the appropriate friction with the flat-shaped engaging portions 38a and 38b can be obtained and its length can be set as the desired length for moving the lens ring 30.

With the structure of the engaging holes 43a and 43b and the structure of the aforesaid flat-shaped engaging portions 38a and 38b, the lens ring 30 can be easily and stably moved on the eyeball as described above.

Further, though the engagement between the lens ring 30 and the connecting portion 42 is described as the engagement between the engaging holes 43a and 43b and the flat-shaped engaging portions 38a and 38b in FIG. 10, it is also a preferable structure to precisely adjust the position using generally-known mechanisms such as the mechanism using the male thread and the female thread, the mechanism using the rack and the pinion, or the like.

Incidentally, the shape of the lens ring 30 is not limited to a substantially cylindrical shape shown in FIG. 10 and may be the elliptic shape or the polygonal shape as described in the description of the holding apparatus 1.

As material of the connecting portion 42, as that of the pair of connecting portions 40a and 40b used in the holding apparatus 1, rubber materials such as silicone rubber, fluorine rubber, natural rubber, SBR, IR, butyl rubber, and neoprene rubber, or resin materials, for example, methacrylic resins such as polymethyl methacrylate, a polycarbonate resin, fluorine resins such as polytetrafluoroethylene, a polyimide resin, and other variety of thermosetting and thermoplastic resins, or suture materials such as a silk suture, or metallic materials such as stainless steel, aluminum, titanium, iron, copper, silver, gold, platinum, or an alloy including aluminum, titanium, iron, copper, nickel or the like, and so on can be used, and silicone rubber, fluorine rubber, and the like are preferable as the rubber material, stainless steel, aluminum, titanium, and the like are preferable as the metallic material, and polymethyl methacrylate and the like are preferable as the resin material.

In addition, it is also a preferable structure in which the connecting portion 42 is manufactured at a low cost by injection molding or the like using the resin materials or the rubber materials so as to be used as a disposable portion in the surgery.

Next, the holding apparatus 3 will be explained with reference to FIG. 11.

In the holding apparatus 3, the same pair of eyelid opener portions 10a and 10b and spring portion 20 as those described in the above description of the holding apparatuses 1 and 2 can be used and the same supporting portion 42 as that described in the above description of the holding apparatus 2 can be used.

Here the lens ring 30 shown in FIG. 11 will be explained.

A pair of engaging portions 39a and 39b of the lens ring 30 of the holding apparatus 3 are similar to the flat-shaped engaging portions 38a and 38b of the aforesaid holding apparatus 2, but further include folded parts having a shape of a letter "L" after passing through the engaging holes 43a and 43b.

This is a preferable structure in which, with the folded parts, the lens ring 30 is suppressed from being disengaged from the connecting portion 42, for example, even when the lens ring 30 is widely moved on the eyeball. Naturally, the shape of the folded parts for suppressing the disengagement of the lens ring 30 from the connecting portion 42 is not limited to this and, for example, may be a bulge having a shape of a teardrop or the like as long as it does not harm the eyeball.

Meanwhile, the flat-shaped engaging portions 38a and 38b of the holding apparatus 2, which do not include the folded parts, enable the lens ring 30 to be easily disengaged from the connecting portion 42, indicating that it is a preferable structure in the aforesaid triple surgery or the like.

As clearly understood from the above explanations, with the holding apparatuses 1 to 3 having the above-described structures, even when the position of the surgical lens is required to be slightly moved during the surgery, the requirement can be responded by moving the position of the lens ring on the eyeball, which enables the surgeon to easily observe the accurate information in the surgical field so as to perform proper surgery in a short time.

Moreover, the holding apparatuses 1 to 3 according to the present invention can be applied not only to the vitreous body surgery but also to general ophthalmological surgery using a surgical lens and also can be widely applied to consulting and diagnosis in addition to the surgery because the burden on the patient is greatly lessened.

INDUSTRIAL AVAILABILITY

As detailed above, the present invention has invented the holding apparatus for the vitreous body surgical contact lens which is characterized in that it has the eyelid opener portions for pulling and opening the upper eyelid and the lower eyelid in order to hold on the eyeball the surgical lens which is indispensable to the surgery of the vitreous body in the eyeball of the human body, the lens ring for holding the vitreous body surgical contact lens on the eyeball, and the connecting portion for connecting the eyelid opener portions and the lens ring of the vitreous body surgical contact lens, in which the vitreous body surgical contact lens is held on the eyeball. This invention has realized the suppression of the energy and the time of the surgeon from being spent, dramatic reduction in the burden on the eyeball of the patient, and further, the reduction in the possibility of the complication after the surgery.

The invention claimed is:

1. A holding apparatus for holding a vitreous body surgical contact lens on a patients eyeball, comprising:
    an eyelid opener portion having a upper portion that pulls and opens an upper eyelid and a lower portion that pulls and opens a lower eyelid;
    a holding portion that holds the vitreous body surgical contact lens on the eyeball, the holding portion located in an open space between the upper portion and the lower portion; and
    a connecting portion that connects the holding portion and the eyelid opener portion, the connecting portion including an elastic member that extends across at least a portion of the open space so that a position of the holding portion relative to the eyelid opener portion and the eyeball is continuously adjustable during surgery without canceling a connection state of the eyelid opener portion and the holding portion;
    wherein the connecting portion comprises a pair of elastic closed loop members for connecting the holding portion in an adjustable state, the holding portion includes a pair of engaging portions disposed opposite one another on the holding apparatus, and the pair of elastic closed loop members engages with the pair of engaging portions.

2. The holding apparatus for the vitreous body surgical lens according to claim 1, wherein the pair of elastic closed loop members are rubber members having a ring shape.

3. The holding apparatus for the vitreous body surgical lens according to claim 2, wherein at least one or more engaging holes for engaging with the engaging portions of said holding portion for the vitreous body surgical contact lens are provided in the closed loop members having the ring shape.

4. The holding apparatus for the vitreous body surgical lens according to claim 2, wherein a substantially rectangular engaging hole is provided in the closed loop members having the ring shape.

5. The holding apparatus for holding the vitreous body surgical contact lens according to claim 2, wherein the rubber members are silicone rubber members.

* * * * *